US006524864B2

(12) United States Patent
Fernandez Decastro

(10) Patent No.: US 6,524,864 B2
(45) Date of Patent: Feb. 25, 2003

(54) TEST STRIP FOR SIMULTANEOUS DETECTION OF A PLURALITY OF ANALYTES

(76) Inventor: Aurora L. Fernandez Decastro, 70421 Hilltop Rd., Union, MI (US) 49130

( * ) Notice: Subject to any disclaimer, the term of this patent is extended or adjusted under 35 U.S.C. 154(b) by 96 days.

(21) Appl. No.: 09/749,439

(22) Filed: Dec. 28, 2000

(65) Prior Publication Data

US 2002/0086435 A1 Jul. 4, 2002

(51) Int. Cl.⁷ .............................................. G01N 33/49
(52) U.S. Cl. ...................... 436/164; 436/166; 436/169; 436/86; 436/95; 436/98; 422/58; 422/82.05; 422/82.06; 422/82.09
(58) Field of Search ............................. 422/56, 58, 61, 422/82.05, 82.06, 82.09; 436/63, 86, 95, 98, 163, 164, 166, 169

(56) References Cited

U.S. PATENT DOCUMENTS

| 3,907,503 A | * | 9/1975 | Betts et al. ................... 356/39 |
| 4,323,536 A | | 4/1982 | Columbus |
| 5,104,619 A | | 4/1992 | De Castro et al. |
| 5,110,724 A | | 5/1992 | Hewett |
| 5,126,276 A | | 6/1992 | Fish et al. |
| 5,589,399 A | | 12/1996 | Allen et al. |
| 5,656,503 A | | 8/1997 | May et al. |
| 5,798,272 A | | 8/1998 | Allen et al. |

* cited by examiner

Primary Examiner—Lyle A. Alexander
(74) Attorney, Agent, or Firm—Browdy and Neimark, P.L.L.C.

(57) ABSTRACT

A test strip for simultaneously measuring a plurality of analytes in blood or other fluids comprising a plurality of reagent pads containing reagents specific to particular analytes located on a support. Each reagent pad is covered and in close contact with a sample distributing layer and an optional blood filtering layer. Color produced by analytes in the sample is viewed through apertures in the support. The colors of the pads are read simultaneously with an instrument such as a reflectance meter containing individual LED's as light sources for each reagent pad. The intensity of the color of the individual pad can be used to detect semi-quantitative or quantitative concentration of analytes in a sample on site, allowing for quick communication of results to a remote site by electronic means.

30 Claims, 2 Drawing Sheets

TEST STRIP FOR SIMULTANEOUS DETECTION OF A PLURALITY OF ANALYTES

FIELD OF THE INVENTION

The present invention relates to a convenient strip test device capable Qf running several color tests simultaneously using a sample such as serum, plasma, or whole blood and a device capable of detecting and measuring the results simultaneously, thereby, providing the measurement of specific damage to organs due to certain diseases with one on-site simple testing method. This provides rapid communication of results to a site remote from the patient by electronic communication.

BACKGROUND OF THE INVENTION

Medically, it is a great advantage as part of a preventive approach to serious organ or metabolic dysfunction to diagnose the disease or dysfunction early. This health alert can be only accomplished by having a convenient system, which allows frequent testing of analytes associated with disorders or dysfunction of major organs to provide early diagnosis. The preferred testing should provide immediate answers at the patient's site, such as at the physician's office, home by health care professionals, or by self testing, and/or long term care facilities so that serious consequences can be avoided or minimized. For such diagnostic testing, the sample of choice is blood.

In the past, several calorimetric methods have been used in the determination of analytes. The Seralyzer® (Ames division of Miles Labs or Bayer) and Ektachem® (Eastman Kodak) system provide quantitation for the determination of several analytes. However, these systems use serum as a sample, not blood. In these cases, the separation of serum from blood requires centrifugation in a laboratory, which generally cannot be performed at the patient's site. Additionally, the analyzers are large in size and the measurements are not done simultaneously but one at a time.

Similarly the dry-chemistry tests provided by Kyoto Daiichi Kagaku for different analytes, also use serum as a sample. Other early inventions involved the measurement of analytes in serum or plasma, not whole blood, such as U.S. Pat. Nos. 5,798,272 and 5,589,399.

Other inventions related to detection of analytes are described in U.S. Pat. Nos. 4,323,536; 5,126,276, and 5,656,503.

Systems known in the prior art that measure analytes in blood are i-Stat® (I-Stat Inc.) and Reflotron® (Boehringer Mannheim). However, the i-Stat system uses an electrochemical methodology, as opposed to calorimetric. The Reflotron is a rather large and complex analyzer, which provides the test answers one at a time and does not measure several analytes simultaneously.

Another system that measures analyte in whole blood is the Stat-Site® (GDS Technology), disclosed in U.S. Pat. No. 5,104,619. This system however differs from the present invention in the complexity of the device, the system lacks the ability to measure several analytes simultaneously providing the results one test at a time, and the sample application area is very small, making application of the sample difficult and giving potentially inaccurate results if the sample has air bubbles.

U.S. Pat. No. 5,110,724 (Cholestech Corp.) is another system that measures analytes in whole blood. However, the system has several drawbacks for use as a point-of-care diagnostic device. These are, the system is not portable; it has a common light source, therefore, it can only measure one color which limits the type of analytes it can measure; the area for sample application and transport zone is complex, leading to a central blood filtering mechanism which separates plasma or serum from blood with the disadvantage of becoming clogged particularly with a high hematocrit sample. In addition, the blood sample application area is very small making it difficult and inconvenient for sample application and resulting in possibly aborting the test when air bubbles are present.

SUMMARY OF THE INVENTION

It is an object of the present invention to overcome the aforesaid deficiencies in the prior art.

It is another object of the present invention to provide a test strip which can be used with whole blood, serum, or plasma.

It is another object of the present invention to provide a simple, easy to use device to test several analytes simultaneously at the site of the patient so that results can be communicated by electronic means to a remote health care site.

It is a further object of the present invention to provide a convenient device in which placing or application of blood samples from venous or capillary blood, such as from a finger stick or a heel stick is convenient and user friendly, whether the application is direct or with a transferring dropper or device.

It is another object of the present invention to provide a device in which the individual reagent pads for each analyte have optional individual filtering areas, as opposed to a central filtering area, so as to minimize the possibility of clogging when whole blood is analyzed.

It is yet another object of the present invention to provide a reflectance meter that provides an individual light source for each reagent pad, providing an optimal method to detect the color reaction necessary for determining each analyte.

The present invention, surprisingly, overcomes all of the difficulties mentioned above by using a sample distributing layer placed uniformly over the pads to allow convenient sample application and uniform distribution of sample for each and all of the individual test pads. Where whole blood is the sample, a filter is placed uniformly over the pads to ensure that the blood is uniformly filtered. The present invention includes a system for measuring the color change in the reagent pads preferably by use of a hand-held portable meter capable of measuring different wave lengths for each pad, thereby increasing its utility to measure a variety of analytes simultaneously.

The device provides the concentration of analytes in whole blood or other sample by calorimetric methods with ease of sample application. The system consists of a strip type structure and a hand held meter that measures the reflectance of several analytes simultaneously. The system is simple and allows for convenient sample application. The method provides a quick and easy simultaneous measurement of several specific disease related analytes and makes possible frequent checks on overall body functions and immediate communication of such functions by electronic means.

For example, increase in concentration of creatinine and BUN (blood urea nitrogen) in blood serves as a marker of kidney dysfunction, increase in alanine aminotransferase enzyme (ALT) in blood serves as a marker of liver dysfunction, increase or decrease in glucose concentration in blood serves as a marker of pancreatic dysfunction i.e. diabetes, increase in cholesterol level serves as a marker of cardiovascular dysfunction, bilirubin serves as a marker for liver dysfunction, etc. The invention can also be used for on-site required testing of neonates for PKU, galactosemia, $T_4$, etc., which today require sample transfer to remote locations for analysis.

The test strip is constructed (see FIG. 2 and FIG. 3), so that the uppermost surface or layer, which is physical or chemical in nature, to which the sample is applied, distributes the sample uniformly and quickly over the length of the strip, such as polyester filtration media by Reemay or Nylon Mesh. The second surface of the device is an optional blood-filtering layer, (see FIG. 2 and FIG. 3) such as a glass fiber matrix that, due to its porosity, allows the serum or plasma to go through while retaining the particulate blood cells. The filtering matrix or layer, when used, extends over all the reagent pads.

Both these matrices are adhered to the bottom structure, the fourth surface, at both ends, through an adhering area such as double sticking tape. In an alternative configuration, an impermeable top layer with a rectangular opening over all the reagent pads can serve to hold together all the layers, the fifth surface, as shown in FIG. 4 and FIG. 5, by adhering to the bottom (support) layer.

The third surface of the device is composed of individual reagent pads made of bibulous material, such as Whatman 54 type matrices, or other membrane such as polyethylene sulfone that absorb the serum or plasma that gets through the filtering layer. Each individual reagent pad may be composed of one or more layers (FIG. 2 and FIG. 3 show two reagent layers) each containing the chemicals necessary for producing the color reactions of the different blood analytes to be tested. The reagent pads are adhered to the support structure or fourth surface.

The fifth surface, shown in FIG. 4 and FIG. 5, is a support structure, which has a longitudinal aperture over all the reagent pads. This support structure does not interfere in the convenience of sample application of the device. Therefore, using both devices the method is the same consisting of applying the sample anywhere on the diffusion or distribution layer, optional separation of red blood cells in the filtering layer, and letting the serum or plasma pass through the reagent area. Furthermore, when the serum or plasma reacts with the chemicals of the reagent pads, the color is produced and is read through apertures in the bottom structure with any color measuring device, including the eye.

The color measuring device may comprise one light source with several different filters, or a plurality of light sources and appropriate light detectors. The color measuring device may be a reflectance meter with a plurality of light emitting diodes (LED's) as light sources with a detector for each light source.

DETAILED DESCRIPTION OF THE INVENTION

A. Assay Device

Figure 1:
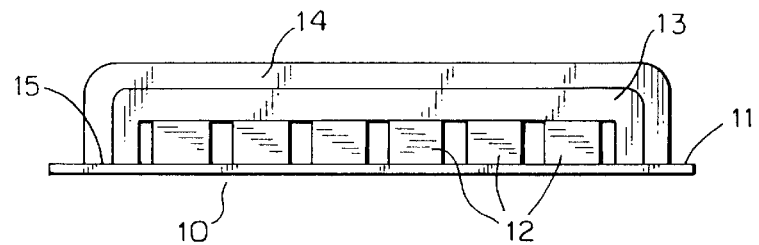
FIG. 1 is a schematic cross-sectional plan view of the device with one support structure.

FIG. 1 illustrates a cross-sectional of the device of the present invention 10 with a support area or layer, generally made of rigid or semi-rigid plastic or other similar material, 11, containing apertures (not shown) under each reagent pad; reagent area or pads 12, and optional filtering area or layer 13; a distribution or diffusion area 14 and adherent area 15.

Figure 2:
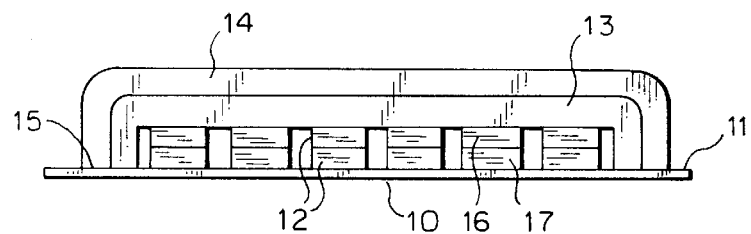
FIG. 2 is a schematic cross-sectional view of the device showing two layers in the reagent area.

FIG. 2 illustrates the same cross sectional view of the device of FIG. 1 showing that the reagent pads can have several layers 16, 17. The illustration shows two layers, 16 and 17, although any number of layers suitable for an assay can be used.

Figure 3:
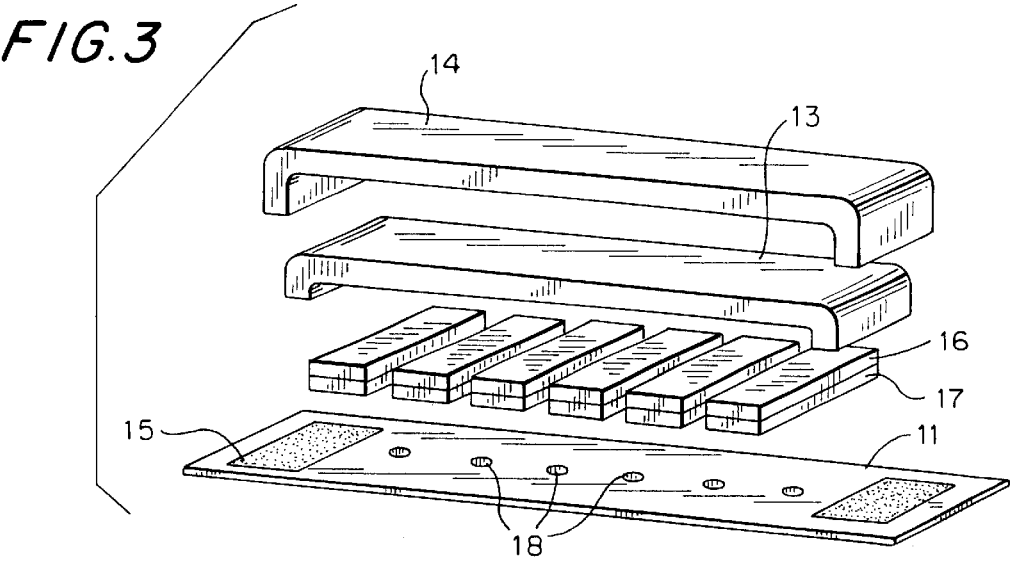
FIG. 3 is a schematic view of the support structure and all layers of the device, showing each layer separately.

FIG. 3 illustrates the structure of FIG. 1 by separating each individual layer. The apertures contained in the plastic support are shown at 18.

Figure 4:
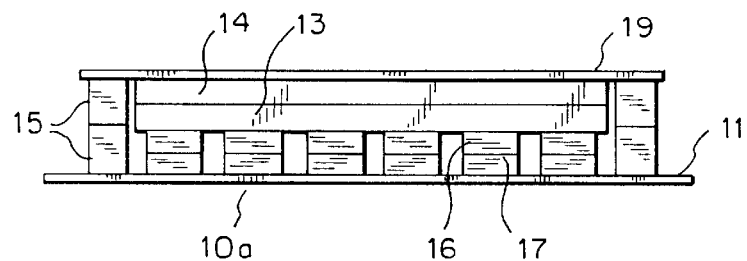
FIG. 4 is a cross-sectional view of another embodiment of the device with top and bottom support structures.
Figure 5:
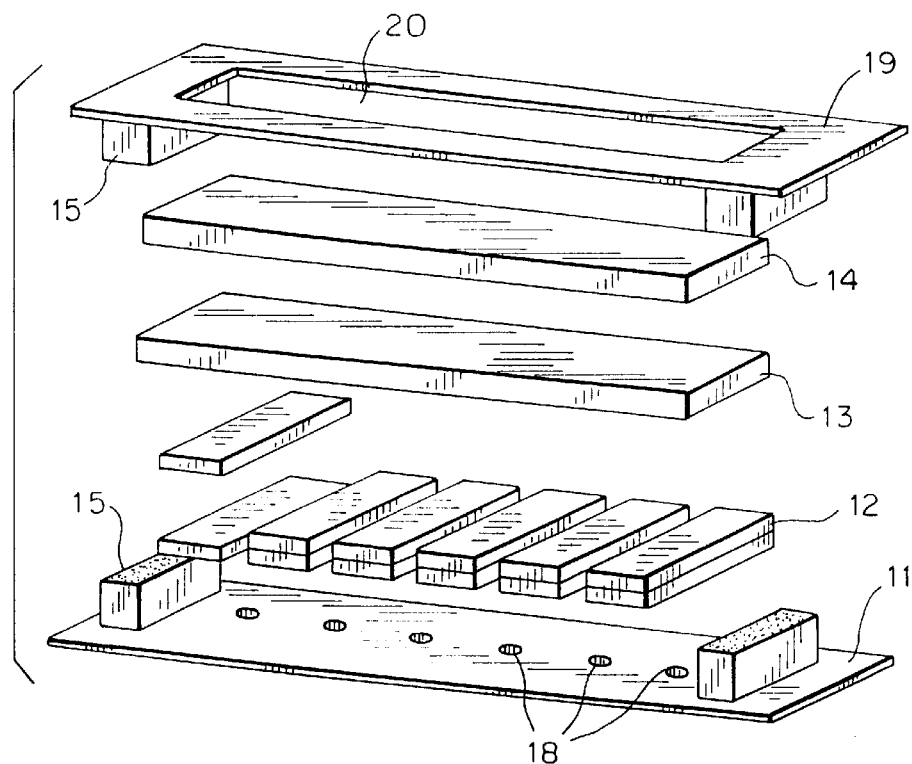
FIG. 5 is a schematic view of another embodiment of the device showing all layers including two holding impermeable structures between which the other functional layers are contained.

FIGS. 4 and 5 show another embodiment, 10a, which illustrates the device having an upper impermeable top support layer 19 or area at the top of the device. This upper area or layer has a lengthwise aperture 20 exposing the distributing layer over all of the reagent pads. The figure illustrates areas of attachment in the top and bottom support layers allowing for the adherence of both support layers to each other.

Figure 6:
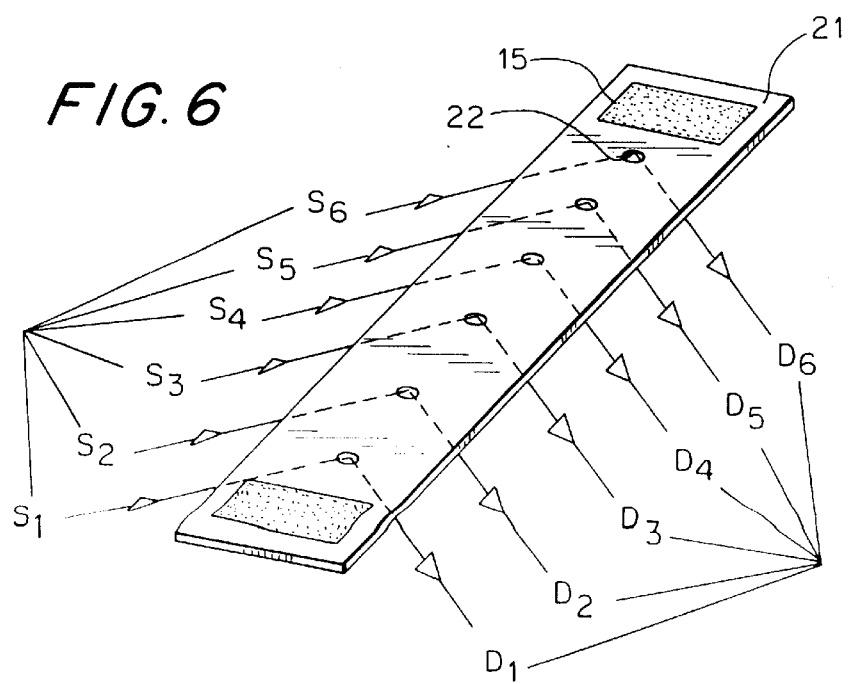
FIG. 6 is a schematic view of the bottom support structure with apertures through which color is exhibited and the multiple light sources and light detectors capable of measuring the intensity of the color through each aperture.

FIG. 6 shows a semirigid structure 21 with six apertures 22, six light sources $S_1$–$S_6$, and six detectors, D1–D6. The number of apertures, sources, and detectors, of course, depends on the number of analytes to be determined, and is not critical to the present invention. FIG. 6 also illustrates a polystyrene plastic strip 21 of about 2–3" length and about 0.15"–0.25" width with circular apertures 22 of about 0.08" to 0.16" in diameter. In a preferred embodiment, for example, the test strip device has a length of 3" with a width of 0.2", which contains six circular apertures of 0.1" that are 0.2" apart from each other for testing of up to six analytes. Each reagent pad (not shown) is 0.12" in diameter adhered over the respective aperture. Individual light sources, such as LED1–LED6, provide light to the device, which is detected by individual detectors D1–D6.

The reagent pads, which are adhered to the support layer by clear adhesive material or other conventional means, are made of bibulous or absorbent materials capable of retaining chemicals, such as Whatman 54 (Whatman) or polyethylenesulfone (PES) membrane (Pall Inc, or Sartorius), containing analytes' specific chemicals dried on the matrix, which can react with each desired blood analyte in a known chemical reaction. The reagent pad having one or more layers, if necessary, separating reactions that require incompatible chemical environments such as acidic or basic conditions.

The reagent pad areas are individually separated from each other by open spaces or plastic protrusions (not shown) between the pads.

The optional filtering area comprises a sieving matrix that by its pore size holds back particulate matter such as red blood cells contained in the blood while allowing the non-particulate serum or plasma to pass through. A variety of matrices on membranes with the approximate pore size in the range of the size of red blood cells are known and can be used for the filtering actions such as glass fiber membranes 0.5 to 8 microns.

By placing the filtering layer lengthwise on the strip each individual pad has its own filtering area directly from the applied blood. This homogenous filtering mechanism of the blood, importantly, allows less opportunity for clogging, as opposed to a central filtering mechanism, even for high hematocrit samples such as neonatal blood.

FIG. 1 illustrates the distribution or diffusion area as the top layer. This layer is specifically designed to break the surface tension of the drop of blood, serum or plasma or other fluid used as a sample. The unity of the drop, resulting from surface tension, collapses when contacting this area, diffusing or spreading the sample across the layer. The higher degree of liquidity of the sample results in better distribution of homogeneity across the optional blood filtering layer and above each individual reagent pad. As a result of the distribution layer, the sample, whether from a finger stick, heel stick, transfer pipette or any other source or application method, can be applied in any location alongside the top layer allowing easier and more convenient sample application.

The distribution layer can be physical in nature such as polyester filtration media by Reemay or nylon mesh, or chemical in nature such as titanium dioxide or barium sulfate, or a combination thereof. Alternatively, these chemicals are applied to the top of the optional filtration layer.

The sample is conveniently applied anywhere on the top layer which disperses and filters. The resulting serum or plasma, after filtration, reacts with reagents to produce color in the reagent pad and the color is detected through the aperture in the bottom support layer. The color can be visually detected or read by any color measuring device such as a reflectance meter consisting of individual LEDs as light sources for each individual reagent pad. The result can then immediately be sent by electronic means to a remote location.

FIG. 6 illustrates the bottom support layer with apertures and light sources such as individual LEDs from 360 nm to 800 nm wavelength and corresponding detectors to measure the color shown through the apertures.

B. Assay method of blood analytes for organ or disease specific tests

It is well known that a variety of tests can be conducted to determine if there is dysfunction or disease in a number of major organs. The system of the present invention can include reagents to conduct assays which provide an overall picture of general health, such as tests for cholesterol, glucose, bilirubin, etc. Alternatively, the system can be designed to test function of only one organ, such as the liver, pancreas, etc.

Known chemical reactions for each organ specific analytes depend on different color formation with different chemicals as illustrated below:

The light sources from 360 nm to 800 nm wavelength of the device allowing for the detection or determination of the colors formed on each reagent pad. The test device measures the color intensity by any measuring system, such as determining the reflectance between 360 and 800 nm wavelength of each reagent pad individually. The color intensity is proportional to the concentration of each analyte. While LEDs are shown as the light source, any conventional light source can be used with any conventional detection device, including the eye.

In a preferred embodiment the test device reaction pads contains chemicals for the determination of several analytes as a General Health Check device or as a watch alert device comprising—BUN (Blood Urea Nitrogen), and creatinine, which are very specific diagnostic marker for kidney related disorders and their levels are increased in such conditions; ALT (alanine amino-transferase) and bilirubin, which are specific diagnostic markers for liver damage (their level increases with the degree of damage of liver); glucose, which is a specific marker for diabetes (its level increases in hyperglycemia and decreases in hypoglycemic state); cholesterol, which is a specific marker for cardiovascular disorders and its increased level is a marker for potential arteriosclerosis.

The reagent pads can have from one to three or more layers.

In the BUN test, the reaction pad contains two reaction layers. The first reaction layer (upper layer) contains ophthaldehyde, in which the reaction of ophthaldedhyde and urea produce 1,3 dihydroxyisoindoline. The lower, second reaction layer contains N-1 naphthyl-diethylenediamine-oxalic acid, which under acidic conditions reacts with 1,3 dihydorxyisoindoline to produce color. Using an LED light source of about 610 nm, the color intensity is measured by reflectance of light, which allows the determination of blood urea nitrogen in a blood sample.

For example, in the creatinine test, the reaction pad has two layers, the upper reaction layer containing lithium hydroxide and the lower reaction layer containing 3,5 dinitrobenzoic acid. The intensity of the color thus produced is measured by a light source comprising of an LED of about 550 nm wavelength.

In another example, the reaction pad for the determination of ALT, the upper reaction layer contains alpha ketoglutarate, alanine, pyruvate oxidase and potassium phosphate, and the lower reaction layer contains peroxidase and 4-amino antipyrine and TOOS to produce magenta color. The light source comprising an LED of about 565 nm wavelength, allows the measurement of ALT.

In yet another example, the reaction pad for the determination of bilirubin consists of one layer with diazonium salt, 2-Methoxy-4-nitrophenyl-diazonium tetrafluoroborate, in presence of dyphylline at low pH. The light source, comprising an LED of about 567 nm wavelength, measures the bilirubin concentration.

In the reaction pad for the determination of glucose, the reaction layer contains glucose oxidase, peroxidase, 4-aminoantipyrine, and phenol. The light source, comprising an LED of about 500 nm wavelength, measures the glucose concentration in blood.

For a cholesterol test, the reaction pad consists of one reaction layer containing cholesterol esterase, cholesterol oxidase, peroxidase, surfactants such as Triton X-1000 and 3, 3,5,5' tetramethylbenzidine. The light source, comprising an LED of about 660 nm wavelength, measures the cholesterol in the sample.

This health check device of up to six analytes can be used with several combinations of analytes to provide the best health care general check. For example, a bilirubin test can be substituted by an albumin or total protein test. In that case, the following example can substitute for one of the six tests mentioned above. In the example of albumin test, the reaction layer contains bromocresolgreen under acidic conditions. The light source, comprising an LED of about 630 nm wavelength, measures the concentration of albumin in whole blood.

For measurement of total protein, the reaction pad contains copper tartrate in the presence of strong alkaline solution of lithium hydroxide. The light source, comprising an LED of about 540 nm wavelength measures the total protein in blood.

The device and method of the present invention also offer quick tests in the area of medical diagnosis for the convenient follow up of a disease related to a particular organ by offering several tests related to that organ or disease. For example, for liver disease, various combination of tests which are markers for different type of liver orders such as alanine aminotransferase (ALT), aspartate aminotransferase (AST), alkaline phosphatase (AP), lactate dehydrogenase (LDH) and bilirubin can be the particular tests of the device.

In this case, the reaction pad for AST comprises L-aspartic acid, alpha ketoglutarate, oxaloacetate carboxylase, phosphate, pyruvate oxidase and 4-aminoantipyrine and DAOS (3,5,dimethoxy-N-ethyl-N-(2-hydroxy-3-sulfopropyl)-aniline sodium salt). AST is measured using an LED light source of about 575 nm.

The reaction pad of alkaline phosphatase (AP) comprises indoxyl phosphate in alkaline conditions, producing a red-violet color. The light source, comprising an LED of about 567 nm wavelength, measures the concentration of AP in the sample.

The reaction pad of lactate dehydrogenase(LDH) comprises lactate, NAD, Nitro Blue Teterazolium salt (NBT) and diaphorase. Using an LED of about 580 nm wavelength the concentration of LDH in blood is obtained.

The reaction pads for aspartate aminotransferase (ALT) and bilirubin have been described above.

Lipid profile analysis contains a various combination of tests, which are markers for different type of cardiovascular disorders such as total cholesterol, high density lipoproteins (HDL), low density lipoproteins (LDL) and triglycerides.

An example of total cholesterol test composition was described above. HDL-Cholesterol is measured by first precipitating LDL with an agent such as dextran on the first layer and allowing HDL to pass through the second layer and reacting with the same reagent layer as for total cholesterol test. This methodology allows the measurement of HDL-Cholesterol.

The difference between total cholesterol and HDL-Cholesterol values yields LDL-cholesterol values.

The reagent pad for determining triglyceride comprises lipoprotein lipase, glycerol kinase, alpha glycerol phosphate oxidase, 4-aminoantipyrine, TOOs and peroxidase. The measurement of triglycerides is made using a light source from an LED of almost 580 nm.

Additionally, a cardiac profile containing various combination of tests, which are markers for heart attacks, include tests such as aspartate aminotransferase(AST), lactate dehydrogenase(LDH), creatinine kinase, creatinine kinase-MB. In this example, the reagent pad for determining creatinine kinase comprises creatinine phosphate, adenine diphosphate, glucose, hexokinase, NADP, glucose-6-phosphate dehydrogenase and tertrazolium violet. An LED of about 550 nm wavelength is used to measure the creatine kinase concentration in the blood sample.

The reagent pad for determination of creatine kinase-MB contains an additional layer on top of the reagent layer for creatine kinase, described above, which is impregnated with antibodies to creatine kinase-MM isoenzyme. This allows the measurement of CK-MB isoenzyme at the same wavelength as creatine kinase.

The AST and LDH tests have been described above.

A group of tests to follow up treatment for kidney disorders may contain reaction pads for BUN, creatinine, protein, albumin and phosphate.

The examples of reagents used for testing BUN, creatinine, protein and albumin have been described above.

In the test for phosphate, the reagent pad contains ammonium molybdate and p-methylaminophenol sulfate at low pH. A light source (LED) of about 680 nm wavelength measures the phosphate in the sample.

A group of tests for electrolyte monitoring contains various combinations of tests such as potassium, sodium, chloride and carbonate. The enzymatic method for the measurement of sodium and potassium is known and employs activation of enzymes specific to sodium or potassium. Alternatively, potassium can also be measured by well known ion selective reaction using a potassium-selective ionophore. The release of a proton is measured as a change in absorption of the dye. For example, the reagent pad is comprised of 7-(N-decyl)-2-methyl-4-('5'-dichlorophen-4' on)-indonaphthol, 2,3-naptho-15-crown-5. A light source of about 640 nm wavelength allows the measurement of potassium.

Chloride can also be determined by measuring the chloride inhibition to specific enzyme such as salicylate hydroxylase. The reaction pad contains salicylate hydroxylase, catechol oxidase and MBTH. A light source (LED) of about 500 nm wavelength measures the chloride concentration in blood.

Similarly, carbon dioxide is measured by known enzymatic reaction. The reagent pad contains phosphoenolpyruvate, PEP carboxylase, thiol-derivative of NADH and measuring oxidized thiol-derivative of NAD at 360 nm wavelength. The light source (LED) of 360 nm wavelength measures the carbon dioxide concentration in blood. Other analytes, such as of determination of PKU, galactosemia, $T_4$, etc. in newborns, can be used in the invention.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

Thus, the expressions "means to . . . " and "means for . . . ", or any method step language, as may be found in the specification above and/or in the claims below, followed by a functional statement, are intended to define and cover whatever structural, physical, chemical, or electrical element or structure, or whatever method step, which may now or in the future exist which carries out the recited functions, whether or not precisely equivalent to the embodiment or embodiments disclosed in the specification above, i.e., other means or steps for carrying out the same function can be used; and it is intended that such expressions be given their broadest interpretation.

What is claimed is:

1. A test strip for simultaneously detecting and measuring more than one analyte in a sample comprising in the following order:

(a) a distribution layer across the length of the test strip wherein a sample can be applied at any spot on the distribution layer which distribution layer breaks the surface tension of a drop of sample and permits uniform distribution of the sample across the distribution layer;

(b) an optional blood filtration layer;

(c) a plurality of reagent pads for each analyte to be measured, wherein each reagent pad containing dry reagents for detection of the analyte to be detected by a specific reagent pad, wherein said reagents produce a change in color proportional to the concentration of the analyte detected in the sample;

(d) a support for the reagent pads wherein changes in the color of the reagent pads can be viewed;

(e) a light measuring device comprising a light source for each reagent pad and a light detector source for each reagent pad enabling simultaneous measurement of each reagent pad.

2. The test strip according to claim 1 further comprising an impermeable top layer over all of the reagent pads, said impermeable top layer being affixed to said support.

3. The test strip according to claim 1 wherein said reagent pads comprise from one to three layers.

4. The test strip according to claim 1 wherein the support for the reagent pads is provided with a single opening for viewing all of the reagent pads.

5. The test strip according to claim 1 wherein the support for the reagent pads is provided with a separate opening for viewing each reagent pad.

6. The test strip according to claim 1 wherein the distribution layer is selected from the group consisting of polyester filtration media, nylon mesh, titanium dioxide, barium sulfate, and combinations thereof.

7. The test strip according to claim 1 containing reagents for measuring analytes selected from the group consisting of blood urea nitrogen, creatinine, glucose, cholesterol, alanine aminotransferase, bilirubin, albumin, total protein, and combinations thereof.

8. The test strip according to claim 1 containing reagents for measuring analytes selected from the group consisting of cholesterol, HDL, LDL, triglycerides, and combinations thereof.

9. The test strip according to claim 1 containing reagents for measuring analytes selected from the group consisting of creatine kinase, creatine kinase-MB, lactate dehydrogenase, aspartate aminotransferase, and combinations thereof.

10. The test strip according to claim 1 containing reagents for measuring analytes selected from the group consisting of bilirubin, alkaline phosphatase, aspartate aminotransferase, alanine aminotransferase, albumin, lactate dehydrogenase, and combinations thereof.

11. The test strip according to claim 1 containing reagents for measuring analytes selected from the group consisting of sodium, potassium chloride, carbon dioxide, and combinations thereof.

12. The test strip according to claim 1 containing reagents for measuring analytes selected from the group consisting of blood urea nitrogen, creatinine, protein, albumin, phosphate, and combinations thereof.

13. The test strip according to claim 1 containing reagents for measuring analytes selected from the group consisting of PKU, galactosemia, $T_4$, and combinations thereof.

14. The test strip according to claim 1 wherein the light sources are light emitting diodes.

15. The test strip according to claim 1 wherein the light measuring device comprises at least one light emitting diode and at least one light detector.

16. A method for simultaneously measuring more than one analyte in a sample comprising:

(a) applying said sample to a test strip by spreading the sample across the top of the test strip, said test strip comprising:
  (i) a distribution layer whereby the sample is uniformly distributed across the zest strip;
  (ii) an optional blood filtration layer;
  (iii) a plurality of reagent pads for each analyte to be measured, wherein each reagent pad contains dry reagents for detection of the analyte to be detected in a specific reagent pad, wherein said reagents produce a change in color proportional to the concentration of the analyte detected in the sample; and
  (iv) a support for the reagent pads wherein changes in the color of the reagent pads can be viewed; and (b) detecting said changes in color simultaneously with a light measuring device wherein each reagent pad has its own light measuring device enabling simultaneous measurement of each reagent pad.

17. The method according to claim 16 wherein the reaction color produced is viewed with light of about 360 to about 800 nm.

18. The method according to claim 16 wherein the sample is whole blood.

19. The method according to claim 16 wherein up to eight analytes are measured for early detection of dysfunction for general health, said analytes being selected from the group consisting of blood urea nitrogen, creatinine, glucose, cholesterol, alanine aminotransferase, bilirubin, total protein, and albumin.

20. The method according to claim 16 wherein the sample is measured for lipid disorders and the analytes are selected from the group consisting of cholesterol, HDL, LDL, triglycerides, and combinations thereof.

21. The method according to claim 16 wherein the sample is measured for cardiac disorders and the analytes are selected from the group consisting of creatine kinase, creatine kinase-MB, lactate dehydrogenase, aspartate aminotransferase, and combinations thereof.

22. The method according to claim 16 wherein the sample is measured for liver disorders and the analytes are selected from the group consisting of bilirubin, alkaline phosphatase, aspartate aminotransferase, alanine aminotransferase, albumin, lactate dehydrogenase, and combinations thereof.

23. The method according to claim 16 wherein the sample is measured for kidney disorders and the analytes are selected from the group consisting of blood urea nitrogen, creatinine, protein, albumin, phosphate, and combinations thereof.

24. The method according to claim 16 wherein the sample is measured for electrolytes selected from the group consisting of sodium, potassium, chloride, and carbon dioxide.

25. The method according to claim 16 wherein the light measuring device comprises a reflectance meter.

26. The method according to claim 16 wherein the light measuring device measures reflected light including a separate light source and a separate light detector for each reagent pad.

27. The method according to claim 18 wherein the whole blood is capillary blood.

28. The method according to claim 27 wherein the capillary blood is obtained from the finger, heel, or earlobe.

29. The method according to claim 16 wherein the color measuring device comprises a reflectance meter with a plurality of light sources and a detector for each reagent pad.

30. The method according to claim 29 wherein the light sources are light emitting diodes.

* * * * *